(12) United States Patent
Roper et al.

(10) Patent No.: US 8,771,330 B1
(45) Date of Patent: Jul. 8, 2014

(54) PERSONAL ARTIFICIAL TRANSPIRATION COOLING SYSTEM

(75) Inventors: Christopher S. Roper, Malibu, CA (US); William B. Carter, Woodland Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 811 days.

(21) Appl. No.: 12/783,542

(22) Filed: May 19, 2010

(51) Int. Cl.
  *A61F 7/00* (2006.01)
(52) U.S. Cl.
  USPC ............... 607/104; 607/96; 607/108; 165/46; 2/458
(58) Field of Classification Search
  USPC .............. 607/96, 104, 108–112, 114; 62/600, 62/606, 614–616, 640, 641; 2/455–458, 2/2.11–2.17; 604/358, 365, 367, 378, 604/385.01
  See application file for complete search history.

(56) References Cited

U.S. PATENT DOCUMENTS

| | | | |
|---|---|---|---|
| 3,783,969 A * | 1/1974 | Pall ................................ | 181/286 |
| 3,906,250 A | 9/1975 | Loeb | |
| 3,984,861 A | 10/1976 | Kessler, Jr. | |
| 4,193,267 A | 3/1980 | Loeb | |
| 4,452,046 A | 6/1984 | Valentin | |
| 4,602,679 A | 7/1986 | Edelstein et al. | |
| 4,673,402 A * | 6/1987 | Weisman et al. ............. | 604/368 |
| 5,238,574 A | 8/1993 | Kawashima | |
| 5,248,079 A | 9/1993 | Li | |
| 6,293,332 B2 | 9/2001 | Li | |
| 6,858,068 B2 * | 2/2005 | Smith et al. ..................... | 96/127 |
| 6,868,898 B2 | 3/2005 | Chau et al. | |
| 6,888,720 B2 | 5/2005 | Pfister et al. | |
| 7,000,682 B2 * | 2/2006 | Chambers ....................... | 165/46 |
| 7,340,898 B2 | 3/2008 | Miller | |
| 7,382,959 B1 | 6/2008 | Jacobsen | |
| 7,401,643 B2 | 7/2008 | Queheillalt et al. | |
| 7,488,547 B1 * | 2/2009 | Iacovelli ........................ | 429/434 |
| 7,513,997 B2 * | 4/2009 | Del Porto ...................... | 210/602 |
| 7,687,132 B1 | 3/2010 | Gross et al. | |
| 8,579,018 B1 | 11/2013 | Roper | |
| 2002/0007201 A1 | 1/2002 | Grahn | |

(Continued)

OTHER PUBLICATIONS

"Fabricating three dimensional nanostructures using two photon lithography in a single exposure step" by Seokwoo Jeon, Viktor Malyarchuk, John A. Rogers, and Gary P. Wiederrecht published in Optics Express, vol. 14, issue 6, at pp. 2300-2308.

(Continued)

*Primary Examiner* — Ahmed Farah
(74) *Attorney, Agent, or Firm* — Ladas & Parry (57) ABSTRACT

A personal artificial transpiration cooling system having a transpiration surface with a substrate, a transpiration membrane layer which is spaced from the substrate layer by one or more spacers to define one or more interior fluid flow channels between a first surface of the transpiration membrane layer and the substrate; and a stoma layer disposed adjacent a second surface of the permeable membrane layer, the stoma layer being spaced from the second surface of permeable membrane layer by a predetermined distance to define one or more cavities disposed between pores in the at least one stoma layer and the second surface of the permeable membrane layer. A fluid reservoir is provided in fluid communication with the one or more interior fluid flow channels, while the transpiration surface is configured to be worn by a human or an animal and the fluid reservoir is designed to be supported, in use, by the human or animal wearing the transpiration surface.

14 Claims, 6 Drawing Sheets

(56) References Cited

U.S. PATENT DOCUMENTS

| | | |
|---|---|---|
| 2005/0202206 A1 | 9/2005 | Wadley et al. |
| 2006/0162907 A1 | 7/2006 | Wu et al. |
| 2006/0163319 A1 | 7/2006 | Ervin et al. |
| 2006/0195179 A1* | 8/2006 | Sun et al. .................. 623/1.54 |
| 2007/0068654 A1 | 3/2007 | Chang |
| 2007/0102140 A1 | 5/2007 | Tuma et al. |
| 2007/0107875 A1 | 5/2007 | Lee et al. |
| 2007/0163755 A1 | 7/2007 | Kim et al. |
| 2010/0157535 A1 | 6/2010 | Oniki et al. |
| 2010/0159398 A1 | 6/2010 | Rock et al. |
| 2010/0264656 A1 | 10/2010 | Flood |

OTHER PUBLICATIONS

Fiber Source. Cellulose. pp. 1-5, [no date]. http://www.fibersource.com/f-tutor/cellulose.htm.

Wheeler and Stroock, "The Transpiration of Water at Negative Pressures in a Synthetic Tree—Supplementary Information"—Nature 10.1038/nature07226.

U.S. Appl. No. 12/783,546, filed May 19, 2010, Roper.

U.S. Appl. No. 12/783,551, filed May 19, 2010, Roper.

U.S. Appl. No. 12/691,393, filed Jan. 21, 2010, Barvosa-Carter.

U.S. Appl. No. 12/383,378, filed Mar. 23, 2009, Roper.

Chen et al. Polymer-Polymer Nanocomposite Membranes as Breathable Barriers with Electro-Sensitive Permeability. Department of Chemical and Biological Engineering, Drexel University, 2009, pp. 1-16.

Enchanted Learning. Leaves and Leaf Anatomy. pp. 1-5, Oct. 2008. http://www.enchantedlearning.com/subjects/plants/leaf/.

"Fabricating three dimensional nanostructures using two photon lithography in a single exposure step" by Seokwoo Jeon, Viktor Malyarchuk, John A. Rogers, and Gary P. Wiederrecht published in Optics Express, vol. 14, issue 6, at pp. 2300-2308, Mar. 20, 2006.

Pages 553-555 of vol. 18, 9th ed. The Encyclopedia Britannica by Thomas Spencer (1888).

Wheeler and Stroock "The transpiration of water at negative pressures in a synthetic tree", Nature vol. 455, pp. 208-212 (2008).

U.S. Appl. No. 12/783,551 (unpublished and non-publication requested), Application and Office Actions, including office action mailed on Jul. 25, 2013.

From U.S. Appl. No. 12/783,551, Office Action mailed on Nov. 7, 2013.

From U.S. Appl. No. 12/383,378 (now U.S. Patent No. 8,579,018), Office Actions including but not limited to Office Actions mailed on Sep. 7, 2012, Feb. 11, 2013, and Jul. 5, 2013.

Carbajal, et al., "Thermal response of a flat heat pipe sandwich structure to a localized heat flux", International Journal of Heat and Mass Transfer, No. 49, (2006), pp. 4070-4081.

Lu, et al., "Active cooling by metallic sandwich structures with periodic cores", Progress in Materials Science, No. 50, (2005), pp. 789-815.

Monro, Tanya M., "Topical review, Catching light in its own trap", Journal of Modern Optics, 2001, vol. 48, No. 2, pp. 191-238.

Queheillalt, et al., "A multifunctional heat pipe sandwich panel structure", International Journal of Heat and Mass Transfer, No. 51, (2008), pp. 312-326.

Tian, et al., "The effects of topology upon fluid-flow and heat-transfer within cellular copper structures", International Journal of Heat and Mass Transfer, Mar. 6, 2004, pp. 1-16.

Jacobsen, et al., U.S. Appl. No. 12/317,210, "Functionally-Graded Three-Dimensional Ordered Open-Cellular Microstructure and Method of Making Same", Application and Office Actions.

Jacobsen, U.S. Appl. No. 11/870,379, "Ordered Open-Cellular Carbon Microstructure and Method of Making Same", Application and Office Actions.

Carter, et al., U.S. Appl. No. 12/691,393, "Microtruss Based Thermal Heat Spreading Structures", Application and Office Actions.

Cumberland, et al., U.S. Appl. No. 12/577,991, "Micro-Truss Based Composite Friction-and-Wear Apparatus and Methods of Manufacturing the Same", Application and Office Actions.

Carter, et al., U.S. Appl. No. 12/691,322, "Microtruss Based Thermal Plane Structures and Microelectronics and Printed Wiring Board Embodiments", Application and Office Actions.

Roper, et al., U.S. Appl. No. 12/405,996, "Ordered Open-Cellular Materials for Mass Transfer and/or Phase Separation Applications", Application and Office Actions.

Roper, et al., U.S. Appl. No. 12/505,980, "Heat Sink Using Micro-Structured Truss", Application and Office Actions.

Roper, et al., U.S. Appl. No. 12/506,014, "Micro-Architected Ordered Cellular Heat Exchangers", Application and Office Actions.

U.S. Appl. No. 12/783,546 (unpublished), Application and Office Actions, including but not limited to the Office Actions mailed on Sep. 5, 2012; Oct. 24, 2012; and Sep. 9, 2013.

U.S. Appl. No. 12/783,551 (unpublished), Application and Office Actions, including but not limited to the Office Action mailed on Jul. 25, 2013.

From U.S. Appl. No. 12/783,546, Office Action mailed on Dec. 18, 2013.

Fiber Source. Cellulose. pp. 1-5, http://www.fibersource.com/f-tutor/cellulose.htm (an office action dated Oct. 24, 2012 from related U.S. case, U.S. Appl. No. 12/783,546).

Meidner. Stomata and Gas Exchange. 1990, (26 pages). http://udspace.udel.edu/bitstream/handle/19716/2830/Chapter%208.%20%3Cstrong%3EStomata%3C/strong%3E%20and%20Gas...?sequence=7.

Wheeler and Stroock "The transpiration of water at negative pressures in a synthetic tree", Nature vol. 455, pp. 208-212 (2008) published together with "The Transpiration of Water at Negative Pressures in a Synthetic Tree—Supplementary Information"—Nature 10.1038/nature07226 (pp. 1-17).

* cited by examiner

PERSONAL ARTIFICIAL TRANSPIRATION COOLING SYSTEM

CROSS REFERENCE TO RELATED APPLICATIONS

This application is related to U.S. patent application Ser. No. 12/783,546 filed on May 19, 2010 and entitled "Artificial Stomata in Artificial Leaves and Methods of Making Artificial Leaves", the disclosure of which is hereby incorporated herein by this reference.

This application is related to U.S. patent application Ser. No. 12/783,551 filed on May 19, 2010 and entitled "Power Generation through Artificial Transpiration", the disclosure of which is hereby incorporated herein by this reference.

This application is related to U.S. patent application Ser. No. 12/691,393 filed on Jan. 21, 2010 and entitled "Mircotruss Bases Thermal Heat Spreading Structures", the disclosure of which is hereby incorporated herein by this reference.

This application is also related to U.S. patent application Ser. No. 12/383,378 filed on Mar. 23, 2009 and entitled "Lightweight Sandwich Panel Heat Pipe", the disclosure of which is hereby incorporated herein by this reference.

TECHNICAL FIELD

Personal artificial transpiration cooling system provides an apparatus for cooling a person or other user. It combines structures that harness thermodynamic energy gradients driven by differences in chemical activity (relative humidity) to enable high surface cooling as well as provide layers of protection from chemical, biological, and/or physical injury for a person or other user (for example, an animal) of the personal artificial transpiration cooling system.

BACKGROUND

Prior art protective suits, whether chemical, biological, physical, armor, etc., inhibit or completely prevent the human (or animal) body's natural cooling mechanism, perspiration, from functioning, which leads to overheating, exhaustion, loss of cognitive function, and eventually death. The disclosed personal artificial transpiration cooling system cools the human (or animal) inside a protective suit to extend the amount of time that human (or animal) can function at a high physical and cognitive level inside the suit. Furthermore, the disclosed personal artificial transpiration cooling system preferably provides this cooling capability in a highly portable manner that does not require external power sources (such as batteries and/or a motor) and their accompanying weight. This cooling capability mimics that of natural perspiration and can even utilize sweat generated by the wearer. Providing an internal environment that removes sweat and provides passive cool temperatures (with preferably noiseless and vibration free operation) will reduce related discomfort, thereby reducing distraction and improving cognitive focus on the wearer's intended task.

A prior art personal cooling system developed at Stanford University and licensed to Avacore (see www.avacore.com) entails cooling a person with liquid water while applying a vacuum to the person's hand. Their system, while effective at rapidly cooling a person, requires an external power supply to achieve the vacuum and circulate the water. This requires power input from an external source (making this scheme not human-portable or impairing mobility) or power input from a human, requiring the energy and attention of the wearer or another individual (making this scheme unsuitable for extended, continuous usage). See also US Patent Publication 2002/0007201 dated Jan. 17, 2002.

The prior art of artificial transpiration includes Wheeler and Strook "The transpiration of water at negative pressures in a synthetic tree", Nature vol. 455, pp. 210-212 (2008) where they demonstrate a system for artificial transpiration using hydrogel membranes. This document does not describe artificial stomata and is therefore limited to operation in environments from 85%-100% relative humidity. At lower relative humidity, cavitation will occur and the system will no longer function. See also Wheeler and Strook, "The Transpiration of Water at Negative Pressures in a Synthetic Tree—Supplementary Information"—Nature 10.1038/nature07226.

BRIEF DESCRIPTION OF THE INVENTION

A personal artificial transpiration cooling system comprising: a transpiration surface having a substrate, a transpiration membrane layer which is spaced from the substrate layer by one or more spacers to define one or more interior fluid flow channels between a first surface of the transpiration membrane layer and the substrate; and a stoma layer disposed adjacent a second surface of the permeable membrane layer, the stoma layer being spaced from the second surface of permeable membrane layer by a predetermined distance to define one or more cavities disposed between pores in the at least one stoma layer and the second surface of the permeable membrane layer; a fluid reservoir in fluid communication with said one or more interior fluid flow channels, the transpiration surface being configured to be worn by a human or an animal and the fluid reservoir being supported in use by the human or animal wearing the transpiration surface.

BRIEF DESCRIPTION OF THE DRAWINGS

FIGS. 6a-6c depict certain embodiments of a human bearing a personal transpiration cooling system. In FIG. 6a the personal transpiration cooling system covers the person's breast (front and/or back). In FIG. 6b the personal transpiration cooling system covers the person's torso (preferably not including their feet, hands or head) preferably over a layer of clothing. In FIG. 6c the personal transpiration cooling system is built into a helmet covering the person's head.

FIGS. 7a-7c depict additional embodiments of a human bearing a personal transpiration cooling system. In FIG. 7a the personal transpiration cooling system covers the person's back. In FIG. 7b the personal transpiration cooling system covers the person's back and utilizes a fluid (typically water) reservoir in fluid communication with the transpiration surface.

FIGS. 8a and 8b depict additional embodiments of a human bearing a personal transpiration cooling system. In FIG. 8a the transpiration surface is preferably mounted on a pack carried by the human. In FIG. 8b the transpiration surface has a plurality of double sided transpiration surfaces which project from the larger transpiration surface adjacent the wearer's back.

DETAILED DESCRIPTION

Wheeler and Strook (identified above) have demonstrated hydrogel membranes which can generate large negative pressures (−6.9 MPa) and allow for net flow of water through a synthetic tree; however, cavitation occurs in their system when the activity (i.e. relative humidity) of the water vapor adjacent to the hydrogel membrane falls below 0.85.

In the second mentioned related patent application identified above, artificial stomata (stomata are pores in, for example, a leaf) which prevent artificial transpiration systems from experiencing cavitation events by controlling the activity (related to the chemical potential) of vapor adjacent to a membrane undergoing artificial transpiration are disclosed.

In the second mentioned related patent application identified above, tree-like structures are provided with large numbers of artificial leaves 10, each of which has a large number of pores or stomata 12.

Figure 1:
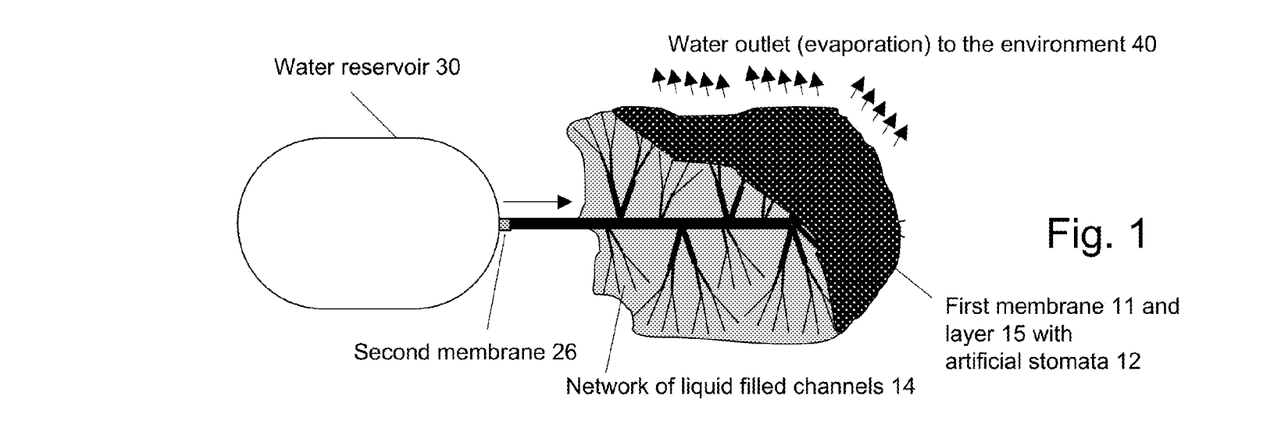
FIG. 1 depicts a schematic diagram of a transpiration cooling system.

A general transpiration cooling architecture is depicted in FIG. 1. The essential features of this architecture include a first membrane 11 which maintains a pressure difference between a liquid on one side of the membrane 11 (which is in fluid communication with liquid in channels 14) and air containing the liquid's vapor on the other (exterior) side of the membrane 11, such that the pressure of the liquid is below that of the vapor. The first membrane 11 is also called an artificial transpiration membrane 11 herein. The liquid is typically water and the vapor is thence typically water vapor, in which case the membrane 11 is preferably a hydrogel membrane. The architecture also includes an interconnected network of liquid filled channels 14. Ideally, there is no vapor present in the channels 14 and the channels should preferably have smooth walls to: (i) reduce pressure loss due to friction (to maximize the allowable distance between the fluid reservoir and the transpiration surface) and (ii) reduce cavitation events, by reducing the number of sites for heterogeneous cavitation events. The architecture also includes artificial stomata 12 (depicted in FIGS. 3 and 4—see the second mentioned US patent application identified above for additional details) if it is desired to operate the system in environments that ever experience less than 85% relative humidity. The architecture also includes second membrane or filter 26 which filters the water drawn into the liquid filled channels 14 to remove vapor bubbles (which could cavitate) and small particles (which could serve as cavitation nucleation sites or could occlude the first membrane).

Transpiration cooling systems are preferably operated in an area with high wind speeds and low humidity.

Optional features of the transpiration cooling architecture include:

(i) Structures and/or check valves may be placed in the liquid filled channels to limit the spread of air embolisms (see the second mentioned US patent application identified above for specifics) including a pump for priming the system with water or re-priming the system after a cavitation/air-embolism event (this could be integrated into the cooling system, but ideally would be a separate piece of equipment used only when necessary and not normally carried by the cooling suit wearer) and providing laminar flow in all regions (no turbulent flow) is preferred to prevent the occurrence of local high velocity flow (which can lead to cavitation).

(ii) Structures enabling the extraction of power from the pressurized water flow may be included. See the schematic view of FIG. 2 where a power generation unit 20 is included (see also the second mentioned US patent application identified above for more specific information).

(iii) The preferred fluid is water, but other fluids could be used instead of water.

(iv) Natural plants and plant parts may be utilized to comprise or fabricate part of the disclosed system. A natural leaf, multiple leaves, or a branch with leaves (all from natural plants or trees) could be used instead of items 12 and 14 in FIGS. 1 and 2, for example. The second membrane 26 would connect the fluid reservoir 30 to the leaf stem, leaf stems, or branch. As stated in the second patent application identified above: a. one could re-prime the limbs and leaves after sealing by pumping liquid (with the priming system which is preferably not always carried by the user); b. one could re-prime lines with gravity driven flow if branches were angled downward; and c. one could do the cutting and installation in a water (or other liquid) bath.

There are a number of limitations to the performance of transpiration cooling systems: (1) The flow of fluid (typically water) will either be heat transfer limited or mass transfer limited. If heat transfer limited, the temperature of the system will drop to a point where the input heat is equal to the heat of vaporization of water times the mass flow rate. If mass transfer limited, the total flow rate will be equal to the maximum mass transfer rate of water vapor from the leaves 12. In this latter case, the flow rate of water will be positively correlated with first membrane area. (2) Damage to the system which results in a hole will lead to the formation of an air embolism which will block fluid flow (air embolism suppression regions will preferably prevent such embolisms from spreading).

Figure 2:
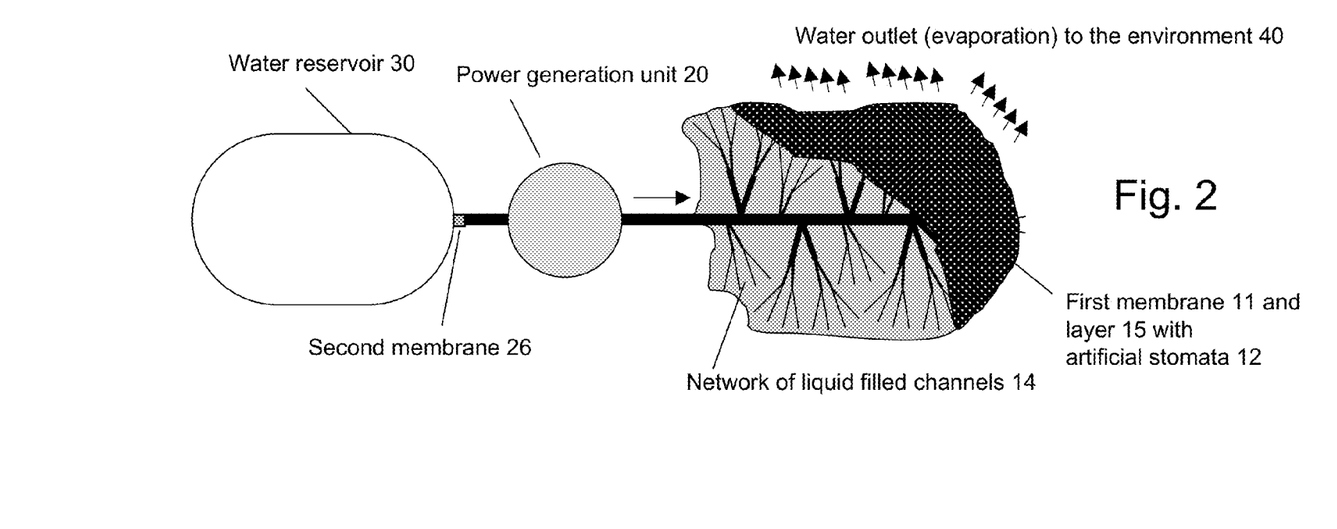
FIG. 2 depicts a schematic diagram of a transpiration cooling system incorporating a power generating unit.
Figure 3:
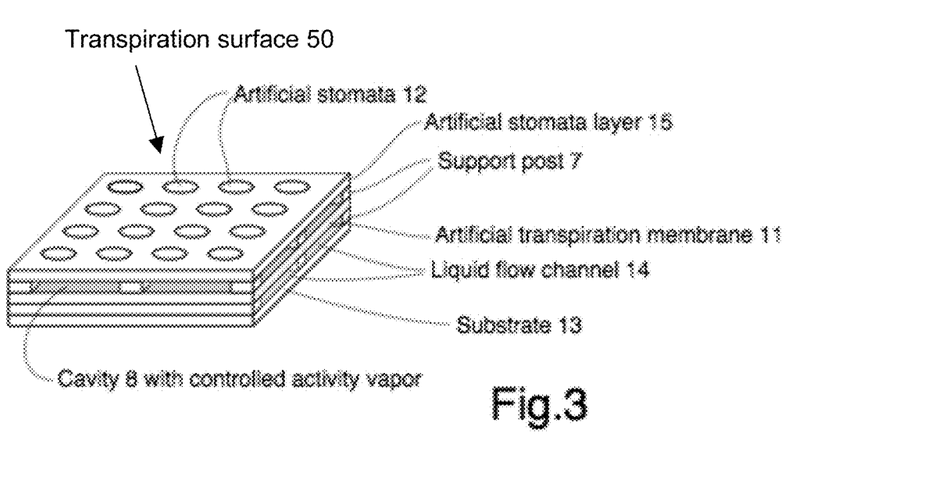
FIG. 3 depicts a section of one embodiment of a single-sided artificial leaf or membrane with artificial stomata.
Figure 4:
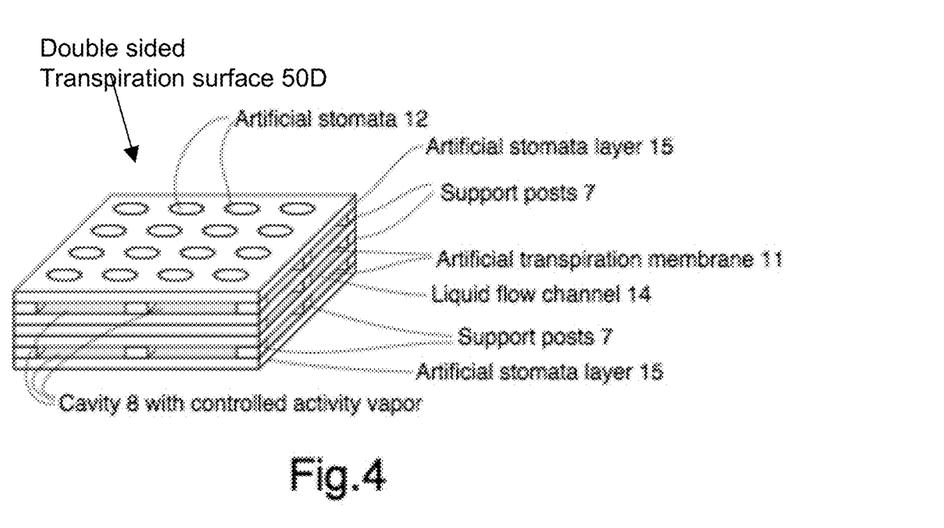
FIG. 4 depicts a section of one embodiment of a double-sided artificial leaf or membrane with artificial stomata.

FIGS. 3 and 4 depict greatly magnified portions of the transpiration surface 50 which acts much like a leaf of a plant. The transpiration surface 50 has an associated network of liquid filled channels 14 shown in FIGS. 1 and 2. It is perhaps best to think of the larger flow channels of FIGS. 1 and 2 in the transpiration surface 50 as being the superhighways for fluid flow that branch down into smaller and smaller flow channels or capillaries 14, the tips of which connect fluid-wise with flow channels 14 in structures like those shown in FIGS. 3 and 4. So the flow channels form a hierarchy from a relatively few relatively large diameter flow channels down to a relatively large number of relatively small diameter flow channels or capillaries where the stomata 12 and associated cavities 8 connect with them. The transpiration surface 50 may be configured as one large leaf 10 or as a plurality of leaves 10 as taught by the second mentioned US patent application identified above.

Artificial leaves 10 or the transpiration surface 50, each with an artificial stoma layer 15, can be single-sided as shown in FIG. 3 or the transpiration surface 50D may be double sided as shown in FIG. 4. If the artificial leaves 10 or transpiration surface 50D is double-sided, the fluid-channel 14 may be centrally located within the leaf 10 or transpiration surface 50D to service stomata 12 on both sides of the artificial leaf 10 or transpiration surface 50D. If the transpiration surface 50D is double sided, then it may be worn, for example, as a cape or as an extended surface or surfaces as depicted by FIG. 8b.

The transpiration surface 50 or 50D has interconnected network of liquid filled channels and capillaries 14 and the channels and capillaries are preferably filled with liquid water. Ideally, in use, there is no water vapor present in the channels or capillaries 14 since the presence of water vapor would be an indication of undesirable cavitation event(s). The transpiration surface 50 has a membrane 11 adjacent to the liquid filled channels 14 on one side thereof and adjacent the cavities on an opposing side thereof. When used with water in the channels 14, the membrane 11 is preferably a hydrogel membrane. One or more cavities 8 are disposed on the other side of the membrane from the liquid filled channels 14 and, in use, are vapor filled due to passage of molecules of the liquid in channels 14 through the membrane and into the cavities 8. The pores 12 in the cavities 8 which vent to the ambient environment 40 (usually air) should be sized so that the vapor activity in the cavities 8 is greater than that required to avoid cavitation in the liquid filled channel 14. The pores can be either static, active, self-regulating or smart.

The possible sizes of the pores, the adjacent fluid channels and the membrane are set forth in the table below, which includes a preferred range of sizes, a reasonable range of sizes and what are presently considered to be the maximum possible ranges of sizes. If no preferred range is stated, then the reasonable range is the preferred range.

|  | preferred range | reasonable range | maximum extents |
| --- | --- | --- | --- |
| Hydrogel membrane 11 thickness | 1 mm | 100 μm-3 mm | 1 μm-5 mm |
| Fluid channel 14 height |  | 100 μm-1 mm | 10 μm-5 mm |
| Fluid channel 14 width |  | 100 μm-1 mm | 5 μm-10 mm |
| Pore 12 diameter |  | 5-200 microns | 1 nm-1 mm |
| Pore 12 pitch |  | 1-100 × pore diameter | 1-10$^6$ × pore diameter |
| Pore 12 depth |  | 0.1 to 10 × pore diameter | 0.01 to 1000 × pore diameter |
| Cavity 8 height |  | 100 microns-1 mm | 0-5 mm |

In some embodiments the cavity 8 can have a zero height cavity meaning that the stoma or pores 12 in the artificial stoma layer 15 are disposed immediately adjacent the artificial transpiration membrane layer 11. See FIG. 5 of the first mentioned US patent application identified above.

Static pores 12 can formed in a stoma layer 15 using molded polymers, punctured polymers, wire mesh, zeolites, porous solids, solid foams, cellular materials, porous anodic alumina, etc.

Active pores 12 are controlled with an input signal for adjusting the pore size or diameter. For example, a perforated electro-active polymer 23 with pores 12 that close upon application of an applied voltage to electrode layers 25 and open when the voltage is removed may be utilized as the stoma layer 15. Alternatively, the size of pores 12 can be controlled with temperature (e.g. the localized heating of a bimetallic strip). Or the pores 12 can be formed from thin-film shape memory alloys with shape controlled by heating, voltage or local temperature.

The substrate 13 shown in FIG. 3 should be non-permeable to the liquid used in the channels 14. Ideally some flexible, lightweight material (a polymer, perhaps polydimethylsiloxane (PDMS)) may be utilized as the substrate 13.

Figure 5:
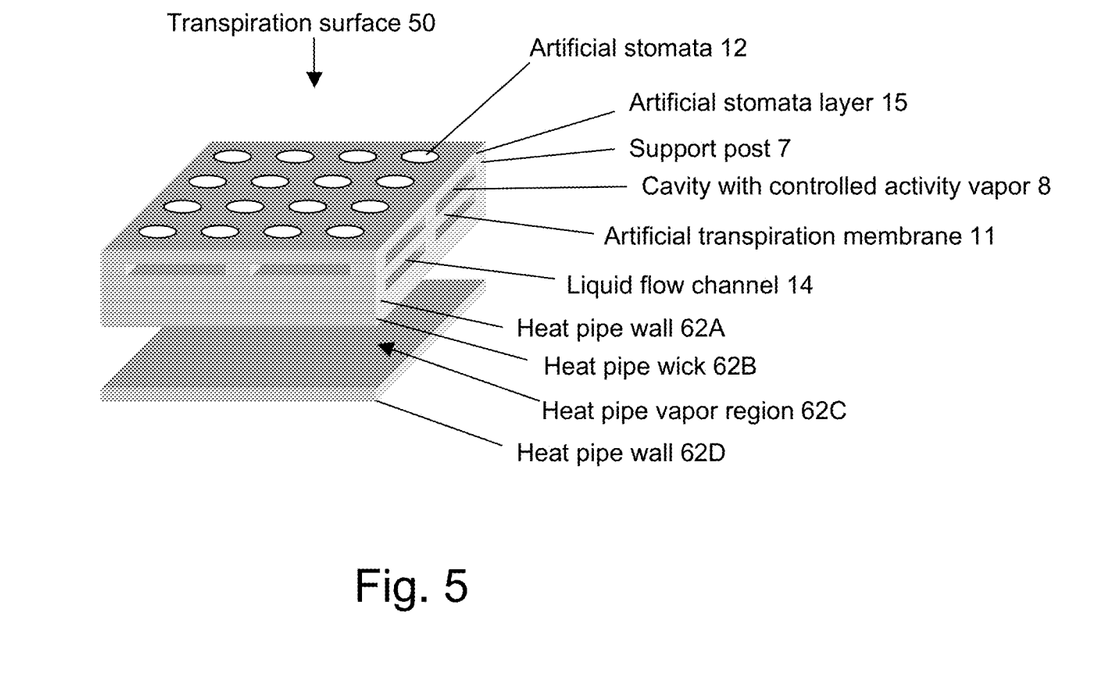
FIG. 5 depicts a section of another one embodiment of a single-sided artificial leaf or membrane with artificial stomata where the single-sided artificial leaf or membrane is disposed in heat transfer relationship with the condensing region of a heat pipe.

The embodiment of FIG. 5 is similar to FIG. 3 in that the stoma 12 occur on one side of the structure, but in this embodiment of the transpiration surface 50 the substrate 13 of FIG. 3 is provided by condensing region of a heat pipe 62. The heat pipe 62 is utilized to provide cooling to human (or other wearer) of a transpiration cooling suit. See the embodiments of FIGS. 7a-7c which are discussed below. In this embodiment, the interior wall 62A of the heat pipe 62 in the heat pipe condenser region is preferably formed by a portion of the artificial leaf so that the working fluid in the heat pipe vapor region 62C condenses directly on the backside of the artificial leaf. The vapor region 62C is defined by two walls, 62A and 62D. A heat pipe wick 62 may be used. The vapor region 62C may contain a porous spacer which could be provided by a microtruss such as that disclosed by U.S. patent application Ser. No. 12/691,393 noted above.

Heat pipes 62 preferably have an internal ordered porosity (for lower pressure drop, and thereby increased heat pipe performance) and minimal weight (which is important for portable applications, such as the Personal Artificial Transpiration Cooling System disclosed herein). The heat pipes 62 could instead have other materials inside to act as a spacer, or have walls designed such that no spacer is required. These later options would be heavier than a heat pipe with a microtruss core, but would cost less to manufacture, and may be preferred compared to a microtruss design.

See also U.S. patent application Ser. No. 12/282,378, also noted above, for another design of a heat pipe which my be utilized, if desired.

Application of the general transpiration cooling architecture into a transpiration cooling system or suit 10 is depicted in FIGS. 6a, 6b, 6c, 7a, 7b, 7c, 8a and 8b. A personal transpiration cooling system or suit is essentially a transpiration surface 50 configured to be worn by a person (or possibly an animal). In order to function as a cooling suit 10 it is preferable that: (1) the transpiration surface 50 be positioned externally of any layers of protection (such as chemical or biohazard protection or armor protection 58) and/or clothing 60; (2) the water reservoir 30 associated with the transpiration surface 50 be located internally or externally to any layers of protection 58 and/or clothing 60; (3) the system be lightweight (so the use of polymer materials is preferred); (4) the transpiration surface 50 be in good thermal contact with the person or animal wearing the transpiration cooling system or suit; and (5) the aforementioned components be flexible (again emphasizing the preference for polymer materials). The reservoir 30 may be located externally of or internally of the persons clothing 60 or the chemical or biohazard protection suit 58. Each location has advantages and disadvantages. A external reservoir 30 is easy to fill and does not require a fluidic via 64 through the protection 58/60, but the water reservoir 30 is not protected as much (i.e. could it be more easily ruptured). An internal reservoir 30 is more difficult to fill and requires a fluidic via 64 through the protection 58, 60, but is protected by the same protective suit 58, 60 that protects the human (or animal) wearer.

Figure 6A:
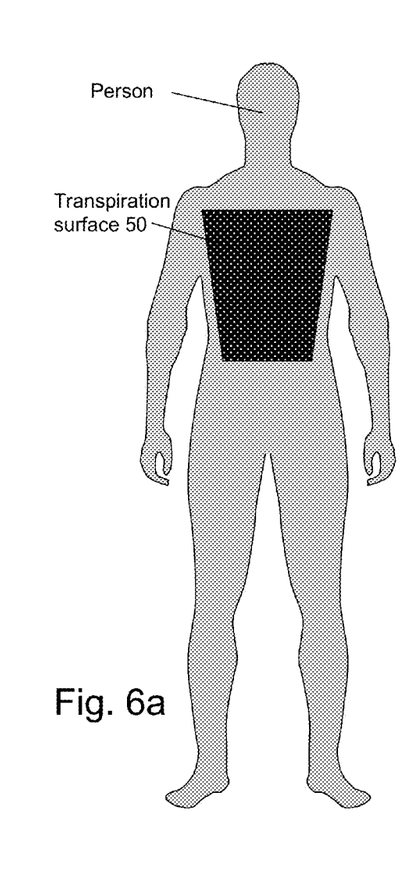
Figure 6B:
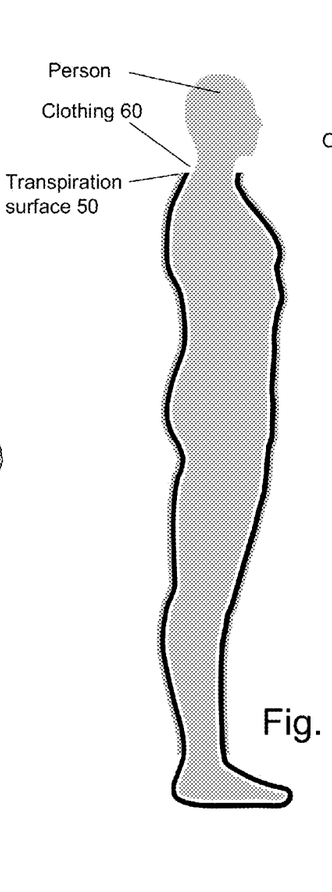
Figure 6C:
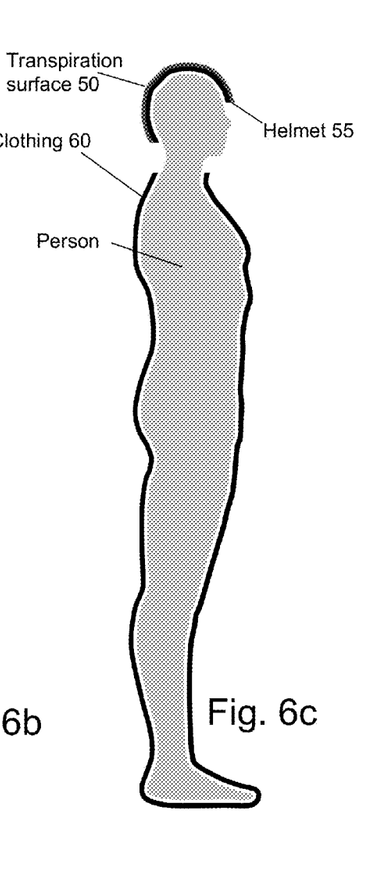

FIGS. 6a-6c depict a human wearing certain embodiments of a personal transpiration cooling system or suit having a transpiration surface 50. In FIG. 6a the personal transpiration cooling system 10 and surface 50 cover the person's breast (front) and/or back. In FIG. 6b the personal transpiration cooling system 10 and surface 50 cover the person's torso (preferably not including their feet, hands or head), but preferably over a layer of clothing 60. In FIG. 6c the personal transpiration cooling system 10 and surface 50 are built into a helmet 15 covering the person's head.

Figure 7A:
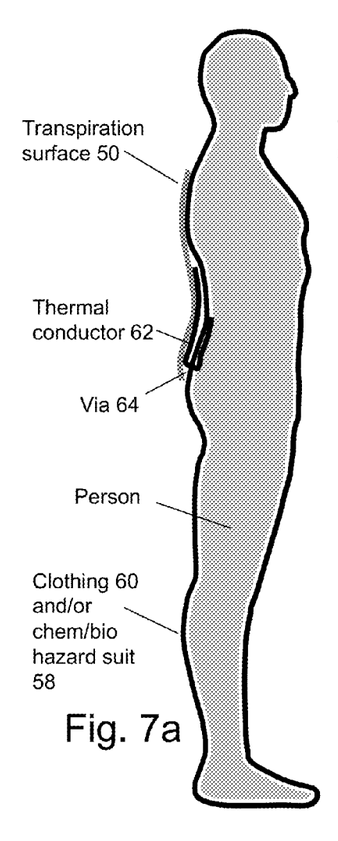
Figure 7B:
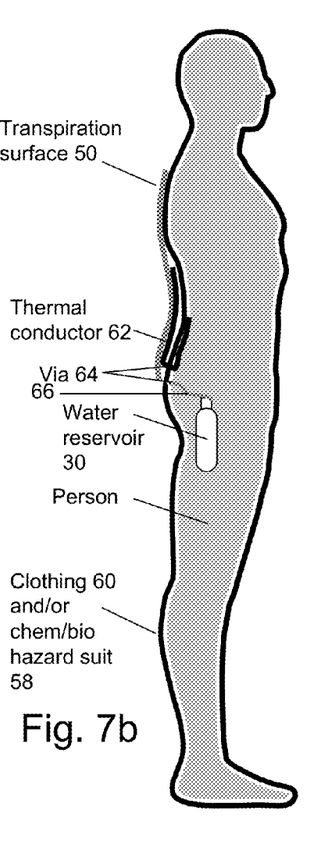
Figure 7C:
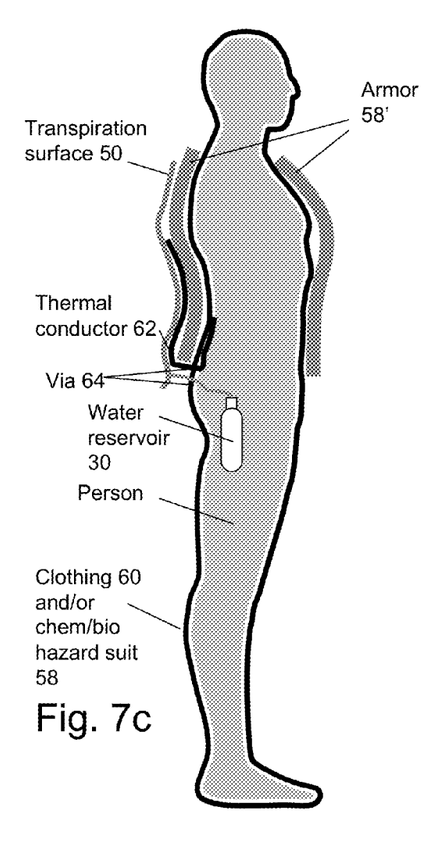
In FIG. 7c the personal transpiration cooling system is similar to the embodiment of FIG. 7b but also includes armor (which might be a bullet proof vest) to which the transpiration surface is attached.

FIGS. 7a-7c depict a human wearing additional embodiments of a personal transpiration cooling system 10 having a transpiration surface 50 and where the human is wearing clothing 60 and/or a chemical or bio-hazard suit 58 which provides thermal isolation for the human from the surrounding exterior environment. The thermal isolation is sometimes needed and therefore desirable and other times it is just an undesirable side effect of wearing the chemical or bio-hazard suit 58. The personal transpiration cooling system 10 is intended to keep the human or other wearer from overheating due to this thermal isolation.

In FIG. 7a the personal transpiration cooling system 10 has a transpiration surface 50 which covers all or most of the human's back. A thermal conductor or heat pipe 62 provides cooling to the human (or other wearer) interiorly of their clothing 60 and/or chemical or bio-hazard suit 58. The thermal conductor or heat pipe 62 enters past the thermal isolation of the human (or other wearer) and enters into a region next to the human (or animal) body by passing through a via 64 in clothing 60 and/or chemical or bio-hazard suit 58.

FIG. 7b is similar to FIG. 7a, but also depicts reservoir 30 which is preferably stowed interiorly of the aforementioned thermal protection and is in fluid communication, via a fluid-carrying tube 66, with the transpiration surface, the tube 66 passing through either the aforementioned via 64 or another such via.

In FIG. 7c is similar to FIG. 7b, but armor protection for the human which may be provided in part by the clothing 60 and/or chemical or bio-hazard suit 58 is augmented by additional amour (such as a bullet proof vest) which can then be used to support the transpiration surface 50.

Figure 8A:
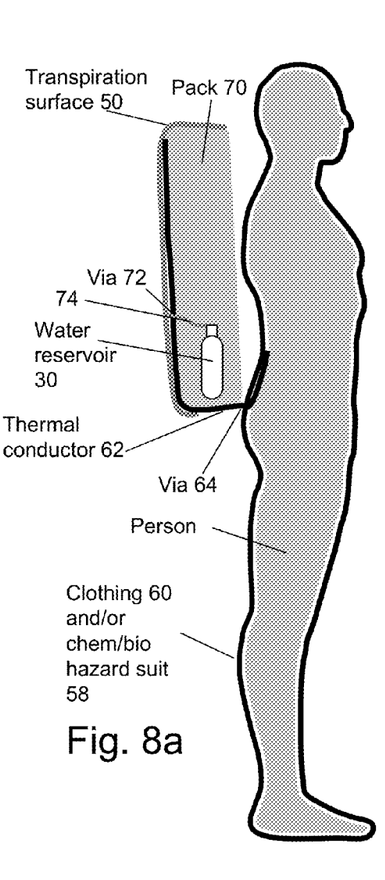
Figure 8B:
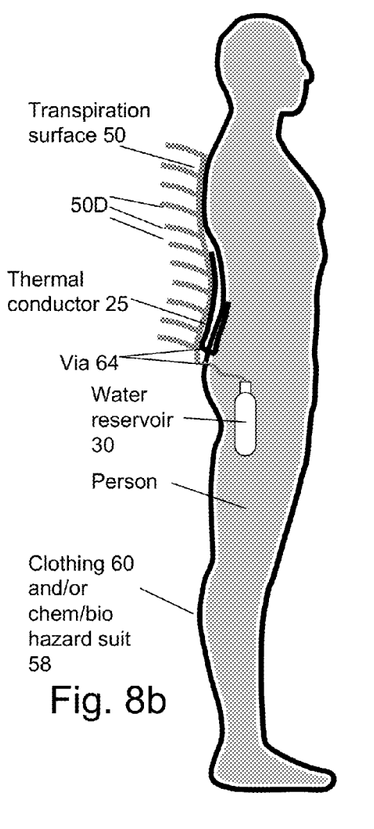

FIGS. 8a and 8b depict a human wearing still additional embodiments of a personal transpiration cooling system 10 having a transpiration surface 50. In FIG. 8a the human is wearing a pack 70 to assist in carrying supplies or equipment needed in a hostile environment. The pack 70 is much like a backpack or a rucksack and optionally made of fire resistant materials. The reservoir 30 may be installed inside the pack 70 as opposed to being located under the human's clothing 60 and/or chemical or bio-hazard suit 58. In such an embodiment the pack 70 has a via 72 to allow a fluid-carrying tube 74 to pass between the reservoir 30 and the transpiration surface 50 mounted on or built into the exterior surfaces of pack 70. The fluid-carrying tube 74 is preferably comprised of a bundle or plurality of tubes arranged in parallel for redundant protection against cavitation and/or rupture.

In FIG. 8b the transpiration surface 50 has a plurality of double sided transpiration surfaces 50D which project from the larger transpiration surface 50. The double sided surfaces 50D preferably have artificial stoma 12 built into both exterior surfaces thereof as shown by FIG. 4.

The transpiration surfaces 50 and 50D have been described with reference to FIGS. 3 and 4. While these embodiments would have a thickness of up to about 5 mm, the material should be sufficiently flexible that the transpiration surface 50 or 50D can be manipulated into desired forms as needed to cover a non-planar surfaces such as the human or animal body (as in the case of the embodiment of FIG. 6b). Or the transpiration surfaces 50 and 50D can be molded in advance to take a pre-selected shape, such as a portion of the human or animal body. If made in large sheets of material and "sewn" like normal cloth, then holes (attachment points for fasteners or for stitching/sewing) would penetrate the entire stack depicted in FIGS. 3 and/or 4. These holes would be situated to not penetrate the liquid flow channel 14. This could be accomplished by designed larger support posts and having the holes run axially through the larger support posts.

Alternatively, a patch of artificial leaf 50 could then be attached (reversibly or irreversibly) with a fastener or stitching through these holes (for example) to an underlying support surface (a suit for the wearer). Or course, the flow channels 14 or the various patches would need to be connected together, but that can be done using tubing similar to tubing 66 used with respect to the reservoir 30 or by just butting two individual pieces of transpiration material 50 together with a suitable adhesive so that the flow channels 14 therein simply communicate between the two aforementioned individual pieces.

Alternatively, a glue or epoxy cement could be used to attach the backside (substrate 13) of the structure in FIG. 3 to the underlying support surface/suit for the wearer. Alternatively a fabric type hook and loop type fastener could be used to attach the substrate 13 side in FIG. 3 to the aforementioned underlying support surface/suit for the wearer—this could be selected regions or across the entire substrate surface 13. In either case the flow channels 14 of the various pieces of material 50 would need to be connected together as shown in FIG. 1 or 2 and discussed above and otherwise sealed to prevent passage of the fluid therein to ambient (other than via the stoma 14).

The thermal conductor 62 is preferably used to transport heat from the wearer, through a via 64 and to the transpiring surface 50 as shown in the embodiments of FIGS. 7a, 7b, 7c, 8a and 8b. Both the heat and the fluid (normally water) need to meet at the transpiration surface 50 for this invention to function effectively. While transpiration drives the fluid flow, a way to drive the heat flow is also important. In the embodiments of FIGS. 6a-6c, placing the transpiration surface either directly on the human (or other wearer) or over clothing that is not particularly thermally insulating, the heat flow may well take care of it self. But if the human or other wearer is wearing thermally insulating materials in the form of clothing or a chemical or bio-hazard suit 58, then a thermally conductive path (such as that provided by thermal conductor 62) between the transpiration surface 50 and the human or other wearer could well be hugely important to the survival of the human (or other wearer). But if the protective suit is thin and not very thermally insulating, then no thermal conductor may be necessary, but for a thick, thermally insulating suit, a thermal conductor 62 will very likely be necessary unless the thermal conduction takes place due to the proximity of the transpiration surface 50 to the skin of the human (or other wearer) such as that provided by the embodiment of FIG. 6b.

The thermal conductor 62, if used, can be a heat pipe, preferably of a flexible type. The heat pipe could be a vapor chamber, a loop heat pipe, a capillary pumped loop or thermosyphon. The thermal conductor 62 could be a solid material of a good thermal conductor (e.g. copper, graphite, aluminum) and even if solid the solid thermal conductor 62 could still be flexible if made of metallic thin foils, bundles of metallic wire, graphene, or carbon nanotubes, for example.]

Optional features of transpiration cooling suits include the ability to use bodily fluids such as sweat, saliva, or urine as a water source for reservoir 30. This requires a membrane, such as membrane 26, which can extract pure liquid water from these fluids. The body fluids could be collected in reservoir 30 or the membrane 26 could be placed directly adjacent to a patch of skin (without reservoir 30) to collect sweat.

The reservoir 30, if used, is preferably readily refillable. The water reservoir 30 need not be a single reservoir, but may be distributed across many areas of the body for weight and balance concerns. Depending of the user's level of activity (i.e. heat generated by body heat), the reservoir should preferably contain between 0.3 and 3 liters of water to provide about four hours of cooling for standard levels of human activity. This does not account for environmental (solar, wind, etc.) heat load or loss, so in a heated environment 40, more reservoir 30 may need to carry even more fluid (normally water). Also complete inactivity or full sprinting would result in lower and higher amounts than the general range given above.

The chemical or bio hazard suit 58 and/or armor 58' may provide layers of protection which convey the ability to completely isolate the wearer from the surrounding environment, including: (i) preventing incident radiation reaching the human or other wearer in doses above approved limits; (ii) preventing undesirable chemicals in the environment from reaching the human or other wearer; (iii) preventing biological and viral materials from reaching the human or other wearer; and/or (iv) preventing physical objects (including projectiles) from harming the human or other wearer.

The transpiration surface 50 may cover (i) some of the body surface area of the wearer; (ii) all of the body surface area of the wearer; (iii) a surface area on an object (e.g. pack 70) carried by or harnessed to the wearer. The transpiration surface 50 may include double-sided embodiments (see element 50D in FIG. 4 and discussed above) allowing additional surface area (e.g. in the form of leaves or flaps) to be attached to the suit (thus increasing the surface area beyond that of the usual body surface area of the wearer). These additional surface areas may extend from body at all times or at only certain times (e.g. they may be mounted on stiff supports, or may be loose flaps which extend in the wind, or they may be actively deployed, when desired). See, for example, the embodiment of FIG. 8b.

Having described the invention in connection with certain embodiments thereof, modification will now suggest itself to those skilled in the art. As such, the invention is not to be limited to the disclosed embodiments except as is specifically required by the appended claims.

What is claimed is:

1. A personal artificial transpiration cooling system comprising:
   a transpiration surface having a substrate, a permeable transpiration membrane layer which is spaced from the substrate by one or more spacers to define one or more interior fluid flow channels between a first surface of the permeable transpiration membrane layer and the substrate; and
   a stoma layer disposed adjacent a second surface of the permeable transpiration membrane layer, the stoma layer being spaced from the second surface of permeable transpiration membrane layer by a predetermined distance to define one or more cavities disposed between pores in the at least one stoma layer and the second surface of the permeable transpiration membrane layer;
   the transpiration surface being configured to be worn by a human or an animal.

2. The personal artificial transpiration cooling system of claim 1 wherein the permeable transpiration membrane layer comprises a hydrogel membrane.

3. The personal artificial transpiration cooling system of claim 1 wherein the stoma layer comprises a layer with an array of pores therein and wherein said stoma layer is preferably formed of a polymer material.

4. The personal artificial transpiration cooling system of claim 3 wherein the array of pores in at least one stoma layer have fixed pore sizes.

5. The personal artificial transpiration cooling system of claim 3 wherein the array of pores in at least one stoma layer have active pore sizes which change size in response to an external stimulus.

6. The personal artificial transpiration cooling system of claim 3 wherein the array of pores in at least one stoma layer have active pore sizes which change size in response to a change in the relative humidity to which the transpiration surface is exposed.

7. The personal artificial transpiration cooling system of claim 3 wherein the array of pores in at least one stoma layer have active pore sizes which change size in response to a change in an electrical control signal.

8. The personal artificial transpiration cooling system of claim 3 wherein the pores in the stoma layer are sized so that, in use, with a fluid filling the one or more interior fluid flow channels from a fluid reservoir, the pores which vent the one or more cavities to an ambient environment are sized so that vapor activity in the one or more cavities is greater than that required to avoid cavitation of the liquid in the one or more interior fluid flow channels.

9. The personal artificial transpiration cooling system of claim 8 further including a membrane for extracting pure water from bodily fluids used as a fluid source for said reservoir.

10. The personal artificial transpiration cooling system of claim 1 further including a fluid reservoir in fluid communication with said one or more interior fluid flow channels.

11. The personal artificial transpiration cooling system of claim 10 wherein the fluid reservoir is supported in use by the human or animal wearing the transpiration surface.

12. The personal artificial transpiration cooling system of claim 1 further including a heat pipe for conducing heat away from the human or animal wearer and towards said transpiration surface.

13. The personal artificial transpiration cooling system of claim 1 wherein at least a portion of said transpiration surface is double-sided with stoma located on each exterior major surface thereof.

14. A chemical and/or bio hazard suit comprising:
   (i) a personal artificial transpiration cooling system according to claim 1; and
   (ii) one or more layers of material for isolating the wearer from the wearer's surrounding environment, said one or more layers of material being disposed between the wearer and said personal artificial transpiration cooling system.

* * * * *